(12) United States Patent
Scrable

(10) Patent No.: US 11,998,507 B2
(45) Date of Patent: Jun. 4, 2024

(54) METHOD AND DEVICE FOR RELIEVING BACK, PELVIC, AND/OR SACRAL PAIN DURING CONTRACTIONS, LABOR, AND CHILDBIRTH

(71) Applicant: Tyler Louis Scrable, Golden, CO (US)

(72) Inventor: Tyler Louis Scrable, Golden, CO (US)

(*) Notice: Subject to any disclaimer, the term of this patent is extended or adjusted under 35 U.S.C. 154(b) by 437 days.

(21) Appl. No.: 17/196,716

(22) Filed: Mar. 9, 2021

(65) Prior Publication Data

US 2021/0275395 A1 Sep. 9, 2021

Related U.S. Application Data

(60) Provisional application No. 62/986,784, filed on Mar. 9, 2020.

(51) Int. Cl.
*A61H 39/04* (2006.01)
*A61F 5/00* (2006.01)

(52) U.S. Cl.
CPC ............ *A61H 39/04* (2013.01); *A61F 5/00* (2013.01); *A61H 2201/0192* (2013.01); *A61H 2201/1253* (2013.01); *A61H 2201/1695* (2013.01); *A61H 2205/081* (2013.01); *A61H 2205/088* (2013.01)

(58) Field of Classification Search
CPC .......... A61F 5/00; A61F 5/024; A61H 39/04; A61H 7/001
USPC ............................... 5/623; 602/5, 32, 36, 61
See application file for complete search history.

(56) References Cited

U.S. PATENT DOCUMENTS

| | | | | |
|---|---|---|---|---|
| 356,497 | A * | 1/1887 | Patten | A61F 13/143 602/61 |
| 3,889,664 | A * | 6/1975 | Heuser | A61F 5/024 602/36 |
| 3,926,182 | A * | 12/1975 | Stabholz | A61F 5/024 602/19 |
| 5,489,258 | A * | 2/1996 | Wohnsen | A61G 7/1051 602/5 |
| 6,298,507 | B1 | 10/2001 | Clyburn | |
| 6,311,349 | B1 | 11/2001 | Kazakia et al. | |
| 6,368,296 | B1 | 4/2002 | Eiter et al. | |
| 6,622,324 | B2 | 9/2003 | Vansteenburg et al. | |
| 7,074,201 | B2 * | 7/2006 | Reinecke | A61F 5/024 602/5 |
| 7,815,584 | B2 * | 10/2010 | Stewart, III | A61F 5/028 602/5 |
| 8,382,693 | B1 * | 2/2013 | Guldalian | A61F 5/028 602/5 |

(Continued)

OTHER PUBLICATIONS

Advent Physical Therapy. (Aug. 6, 2019). Pelvic girdle pain treatment: Rockford, MI. Advent Physical Therapy. https://adventpt.com/treatment-for-pelvic-pain-during-pregnancy-in-rockford-mi/#:~:text=Soft%20tissue%20mobilization%20%E2%80%94%20Soft%20tissue,tension%20and%20improve%20your%20flexibility. (Year: 2019).*

(Continued)

*Primary Examiner* — Julian W Woo
*Assistant Examiner* — Osama Nemer
(74) *Attorney, Agent, or Firm* — Peter B. Scull

(57) ABSTRACT

A method and device are provided for relieving back, pelvic, and/or sacral pain during labor, contractions, and/or childbirth, the device and method applying pressure to the pelvic and/or lower back areas of a pregnant woman to relieve the pain caused by contractions, labor, and/or childbirth, and the device can be used by the pregnant woman or a healthcare provider.

19 Claims, 3 Drawing Sheets

(56) References Cited

U.S. PATENT DOCUMENTS

| | | | |
|---|---|---|---|
| 8,784,279 B2 | 7/2014 | Cantrell | |
| 2002/0032397 A1* | 3/2002 | Coligado | A61F 5/028 |
| | | | 602/5 |
| 2005/0234380 A1* | 10/2005 | Fulford | A41D 13/0158 |
| | | | 602/61 |
| 2006/0009726 A1* | 1/2006 | Clement | A61F 13/06 |
| | | | 602/61 |
| 2013/0218062 A1* | 8/2013 | Jung | A61H 1/0222 |
| | | | 602/36 |
| 2015/0133839 A1* | 5/2015 | Roebelt | A61F 5/01 |
| | | | 602/5 |
| 2019/0142685 A1* | 5/2019 | Heller | B25B 5/067 |
| | | | 601/133 |
| 2020/0093629 A1* | 3/2020 | Marko | A61F 5/00 |
| 2021/0236372 A1* | 8/2021 | Carr | A61H 7/001 |
| 2021/0283000 A1* | 9/2021 | Karvandi | A61H 1/006 |
| 2022/0008284 A1* | 1/2022 | Smith | A61H 23/02 |
| 2023/0190569 A1* | 6/2023 | Wallace | A61H 7/003 |
| | | | 601/133 |

OTHER PUBLICATIONS

Oswald, C., Higgins, C. C., & Assimakopoulos, D. (2013). Optimizing pain relief during pregnancy using manual therapy. Canadian family physician Medecin de famille canadien, 59(8), 841-842. (Year: 2013).*

\* cited by examiner

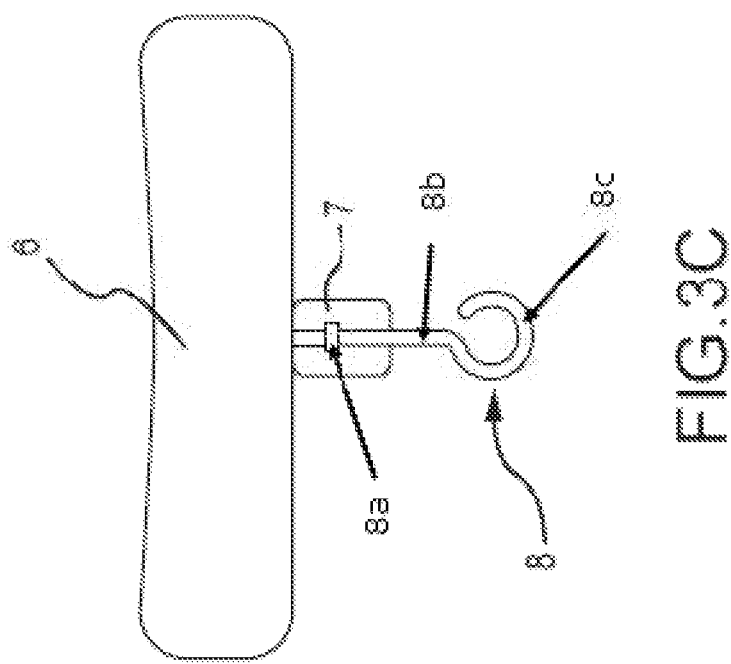
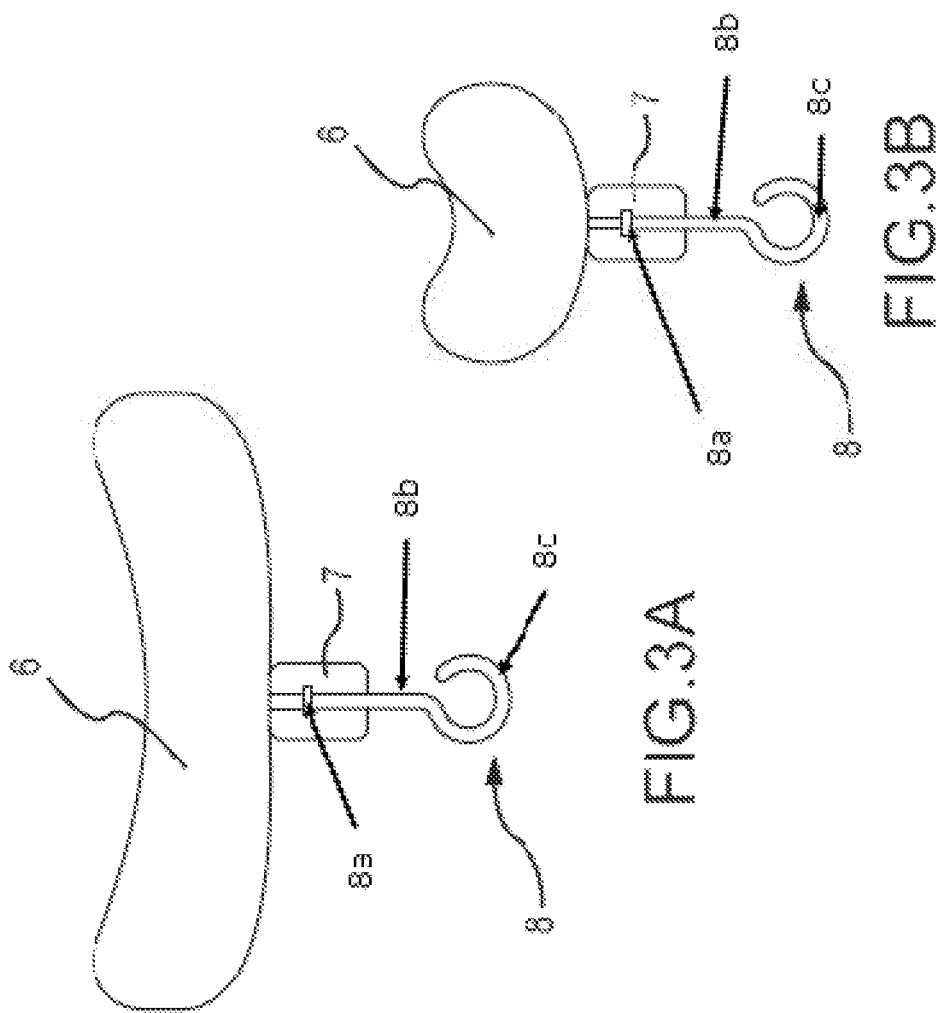
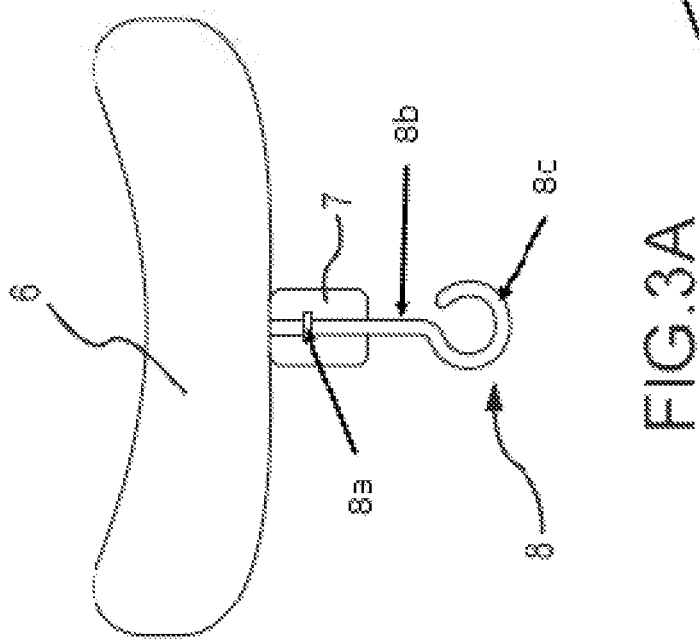

METHOD AND DEVICE FOR RELIEVING BACK, PELVIC, AND/OR SACRAL PAIN DURING CONTRACTIONS, LABOR, AND CHILDBIRTH

FIELD

Disclosed are a method and/or device for relieving back, pelvic, and/or sacral pain during labor, contractions, and/or childbirth.

BACKGROUND

Back, pelvic, and/or sacral pain is/are a very common occurrence that women experience during labor, contractions, and/or childbirth. Oral, IV, subQ, or local injection drugs to reduce this pain are commonly administered during labor, contractions, and/or childbirth. However, these types of therapy have side effects that can lead to unwanted or undesired outcomes in the health, comfort, and/or physiology of the mother and the child or fetus. Accordingly, there is a need to provide alternative labor pain treatments that can avoid some or all of these unwanted or undesired side effects and/or outcomes.

BRIEF SUMMARY

It has been unexpectedly discovered that applying mechanical pressure to the outside of the hips or pelvis, the center of the outside of the hips or pelvis, and/or the rear of the sacrum reduces and/or significantly reduces the sensation of pain during labor, child delivery, and/or contractions. Accordingly, the present disclosure includes a method and/or device for relieving back, pelvic, and/or sacral pain during labor, contractions, and/or childbirth.

In one or more implementations, the developments herein described can optionally include a method for reducing pain in the pelvic and/or lower back area of a woman during contractions, labor, and/or child birth, the method including:
(a) providing a device that applies pressure to pressure points on the outside of the hips or pelvis and/or lower back of a person experiencing pain in the pelvic area and/or lower back areas during labor, wherein the device including:
  (i) a first clamp including a first clamping area; a releasable first trigger; a first sliding mechanism; a first locking mechanism; and a first threaded connection;
  (ii) a second clamp including a second clamping area; a releasable second trigger; a second sliding mechanism; a second locking mechanism; and a second threaded connection;
  (iii) a bar including a sliding area for sliding the first clamp and the second clamp along the length of the bar;
  (iv) a first padding attachment including an interior first threaded tubing threaded onto the first threaded connection of the first clamp; the first threaded tubing covered by a first exterior foam; the first padding attachment operably attachable to the first clamp via the first threaded connection; and
  (v) a second padding attachment including an interior second threaded tubing threaded onto the second threaded connection of the second clamp; the second threaded tubing covered by a second exterior foam; the second padding attachment operably attachable to the second clamp via the second threaded connection; and
  (vi) an adjustable slider including:
    (A) a folded portion slidable along the bar between the first clamp and the second clamp;
    (B) a threaded opening for a threaded bolt;
    (C) a threaded bolt threaded through the threaded opening and having at one end at least one of interchangeable back pressure foam attachments; and having at an opposite end tightening or loosening portions;
  wherein the adjustable slider is configured to apply different pressures to a central portion of the lower back or pelvis to relieve pain in the lower back or pelvis by applying pressure to the one of the interchangeable back pressure foam attachments by tightening or loosening the tightening or loosening portions by turning the threaded bolt within the threaded opening, after the first and second clamps have been positioned to apply the pressure to the pressure points on the outside of the hips or pelvis and/or lower back of the person experiencing the pain in the pelvic area and/or lower back areas during labor; and
(b) applying pressure using the device to the pressure points on the outside of the hips or pelvis and lower back or center rear pelvis of the person experiencing pain in the hips, pelvic, and/or lower back areas during contractions, labor, or childbirth, such that the pain in the hips, pelvis, and/or lower back areas is reduced, wherein the applying pressure includes:
  (i) locking the second clamp adjacent one end of the sliding area of the bar using the releasable second trigger and the second locking mechanism;
  (ii) sliding or providing the adjustable slider over the opposite end of the sliding area of the bar;
  (iii) sliding the first sliding mechanism of the first clamp over the sliding area of the bar using the releasable first trigger and locking the first clamp to the bar using the first locking mechanism, such that the outside of the hips or pelvis are clamped between the first padding attachment and the second padding attachment;
  (vi) tightening or loosening the tightening or loosening portions of the adjustable slider to apply different pressures to the one of the interchangeable back pressure foam attachments, and/or the first padding attachment and the second padding attachment, to the lower back or rear central pelvis, after the first and second clamps have been positioned, such that pressure is applied to the pressure points on the outside of the hips or pelvis and/or lower back or central rear pelvis of the person experiencing the pain in the pelvic area and/or lower back areas during labor, such that the pressure applied reduces pain during contractions, labor, and/or child birth.

In one or more implementations, the developments hereof can optionally include a device for reducing pain in the pelvic and/or lower back area of a woman during contractions, labor, and/or child birth, the device configured for applying pressure to pressure points on the outside of the hips or pelvis and/or lower back of a person experiencing pain in the pelvic area and/or lower back areas during labor, wherein the device includes:
(a) a first clamp including a first clamping area; a releasable first trigger; a first sliding mechanism; a first locking mechanism; and a first threaded connection;

(b) a second clamp including a second clamping area; a releasable second trigger; a second sliding mechanism; a second locking mechanism; and a second threaded connection;
(c) a bar including a sliding area for sliding the first clamp and the second clamp along the length of the bar;
(d) a first padding attachment including an interior first threaded tubing threaded onto the first threaded connection of the first clamp; the first threaded tubing covered by a first exterior foam; the first padding attachment operably attachable to the first clamp via the first threaded connection; and
(e) a second padding attachment including an interior second threaded tubing threaded onto the second threaded connection of the second clamp; the second threaded tubing covered by a second exterior foam; the second padding attachment operably attachable to the second clamp via the second threaded connection; and
(f) an adjustable slider including: (A) a folded portion slidable along the bar between the first clamp and the second clamp; (B) a threaded opening for a threaded bolt; (C) a threaded bolt threaded through the threaded opening and having at one end at least one of interchangeable back pressure foam attachments; and having at an opposite end tightening or loosening portions; wherein the adjustable slider is configured to apply different pressures to a central portion of the lower back or pelvis to relieve pain in the lower back or pelvis by applying pressure to the one of the interchangeable back pressure foam attachments by tightening or loosening the tightening or loosening portions by turning the threaded bolt within the threaded opening, after the first and second clamps have been positioned to apply the pressure to the pressure points on the outside of the hips or pelvis and/or lower back of the person experiencing the pain in the pelvic area and/or lower back areas during labor.

In one or more embodiments, the developments hereof can optionally be configured for applying pressure using the device to the pressure points on the outside of the hips or pelvis and lower back or center rear pelvis of the person experiencing pain in the hips, pelvic, and/or lower back areas during contractions, labor, or childbirth, such that the pain in the hips, pelvis, and/or lower back areas is reduced, wherein the applying pressure includes two or more of: (i) locking the second clamp adjacent one end of the sliding area of the bar using the releasable second trigger and the second locking mechanism; (ii) sliding or providing the adjustable slider over the opposite end of the sliding area of the bar; (iii) sliding the first sliding mechanism of the first clamp over the sliding area of the bar using the releasable first trigger and locking the first clamp to the bar using the first locking mechanism, such that the outside of the hips or pelvis are clamped between the first padding attachment and the second padding attachment; (vi) tightening or loosening the tightening or loosening portions of the adjustable slider to apply different pressures to the one of the interchangeable back pressure foam attachments to the lower back, after the first and second clamps have been positioned, to apply the pressure to the pressure points on the outside of the hips or pelvis and/or lower back of the person experiencing the pain in the pelvic area and/or lower back areas during labor, such that the pressure applied to the outside of the hips or pelvis and the pelvic and/or lower back areas reduces pain during contractions, labor, and/or child birth.

In one or more implementations, the developments hereof can optionally include wherein the bar includes steel.

In one or more implementations, the developments hereof can optionally include wherein the first clamp is configured to slide up and down the bar while the second clamp is fixed to the bar.

In one or more implementations, the developments hereof can optionally include wherein the first or second threaded tubing includes steel.

In one or more implementations, the developments hereof can optionally include wherein the first or the second releasable trigger includes a trigger release to unlock the first or second locking mechanisms.

In one or more implementations, the developments hereof can optionally include wherein the foam of the first or second padding attachments includes polyurethane foam.

In one or more implementations, the developments hereof can optionally include wherein the method further includes the step of (c) heating the lower back, pelvis, or hips of the woman to further reduce the sensation of pain by the woman.

In one or more implementations, the developments hereof can optionally include wherein the method further includes the step of (c) vibrating the lower back, pelvis, or hips of the woman to further reduce the sensation of pain by the woman.

In one or more implementations, the developments hereof can optionally include wherein the bar includes plastic, metal, aluminum, fiberglass, rubber, and/or carbon fiber.

In one or more implementations, the developments hereof can optionally include wherein both the first clamp and the second clamp are configured to slide up and down the bar while the second clamp is fixed to the bar.

In one or more implementations, the developments hereof can optionally include wherein the first or second threaded tubing includes one or more of plastic, metal, aluminum, fiberglass, rubber, and/or carbon fiber.

In one or more implementations, the developments hereof can optionally include wherein the first or the second releasable trigger includes a trigger lock to lock the first or second trigger and/or locking mechanisms.

In one or more implementations, the developments hereof can optionally include wherein the foam of the first and/or second padding attachments includes one or more of an open cell foam, a plastic foam, a polymer foam, and/or a compostable foam.

In one or more implementations, the developments hereof can optionally include wherein the step (c) heating the lower back, pelvis, or hips of the woman to further reduce the sensation of pain by the woman includes applying one or more of dry, wet, or infrared heat.

In one or more implementations, the developments hereof can optionally include wherein the step (c) vibrating the lower back, pelvis, or hips of the woman to further reduce the sensation of pain by the woman includes sonic, mechanical, or infrared vibration.

In one or more implementations, the developments hereof can optionally include wherein the pressure is applied for a period of 1 to 120 minutes.

In one or more implementations, the developments hereof can optionally include wherein the pressure is applied for a period of 1 to 30 hours.

In one or more implementations, the developments hereof can optionally include wherein the first clamp slides towards the second clamp to create pressure on the outside of the hips or pelvis.

In one or more implementations, the developments hereof can optionally include wherein the first clamp uses a first trigger to create pressure on the outside of the hips or pelvis.

In one or more implementations, the developments hereof can optionally include wherein the first trigger includes a quick release lever to reduce pressure from the first and/or second clamps to the outside of the hips or pelvis.

In one or more implementations, the developments hereof can optionally include wherein the first and/or second padding attachments can be interchanged with padding attachments having different angles to provide different angles and/or amounts of pressure from the first and/or second clamps to the outside of the hips or pelvis.

In one or more implementations, the developments hereof can optionally include wherein the back pressure attachments (6) can be tightened/loosened via a threaded bolt. The clamp (1) can be flipped so the device can be used by the subject without the need for assistance.

The foregoing and other objects and aspects of the present developments hereof are explained in greater detail in the drawings herein and the specification set forth below. The disclosures of all United States Patent references cited herein are to be incorporated by reference herein in their entirety.

BRIEF DESCRIPTION OF THE DRAWINGS

FIG. 3A shows a first non-limiting example of the adjustable slider in a top view.

FIG. 3B shows a second non-limiting example of the adjustable slider in a top view.

FIG. 3C shows a third non-limiting example of the adjustable slider in a top view.

DETAILED DESCRIPTION

Figure 1:
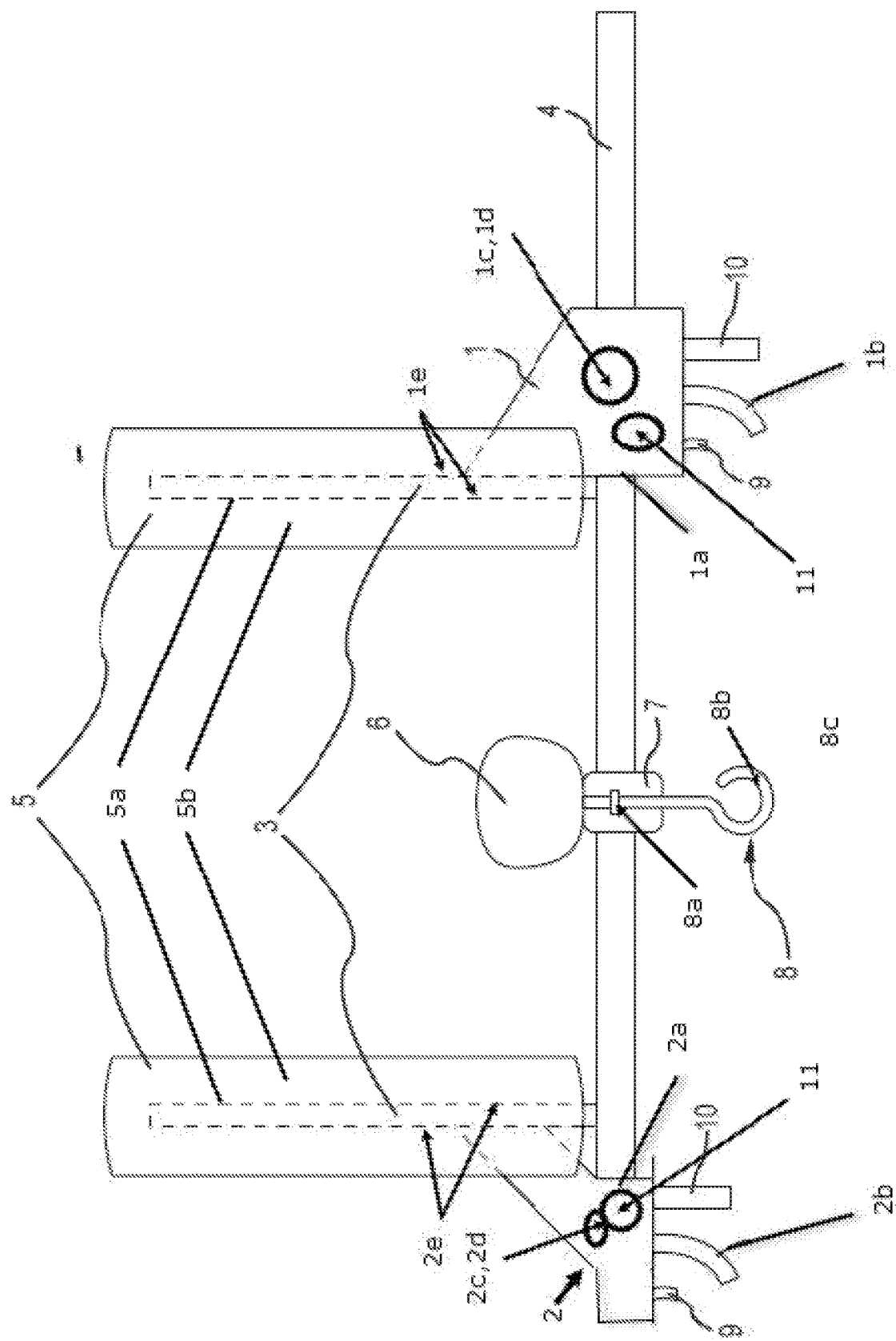
FIG. 1 shows a non-limiting example of the entire device in an extended view.
Figure 2:
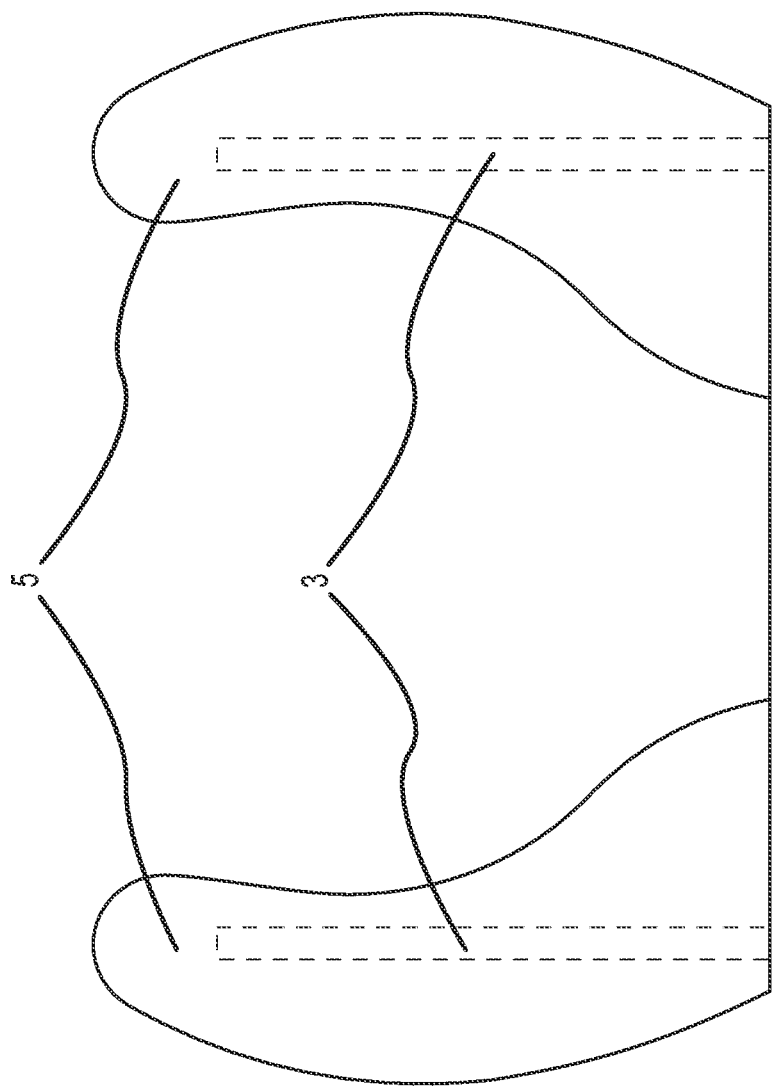
FIG. 2 shows a non-limiting example of a front perspective view of the device.

It has been unexpectedly discovered that applying mechanical pressure to the outside of the hips or pelvis, the center of the outside of the hips or pelvis, and/or the rear of the sacrum reduces and/or significantly reduces the sensation of pain during labor, child delivery, and/or contractions. Accordingly, the present developments hereof include a method and/or device for relieving back, pelvic, and/or sacral pain during labor, contractions, and/or childbirth.

FIGS. 1, 2, 3A, 3B and 3C show a non-limiting example of the entire device in an extended view including a first clamp (1); a second clamp (2); first and second threaded tubing (3); a bar (4); first and second padding attachments (5); interchangeable back pressure foam attachments (6); a folded portion (7) a threaded opening; a threaded bolt (8b) that screws into the threaded opening (8a) of folded portion (7), a trigger release (9), a handle (10), and a trigger system (11).

The first and second threaded tubing (3) and padding surrounding; include the first and second padding attachments (5), respectively. The interchangeable back pressure foam attachments (6); the folded portion (7); and the threaded opening (8a) include an adjustable slider (6/7/8).

The first clamp (1) and the second clamp (2), connected to first and second threaded tubing (3) covered by first and second padding attachments (5), are configured to slide along the bar (4) in sliding area (4a), such as a channel or groove provided in the bar (4), with the adjustable slider (6)/(7)/(8) therebetween, as shown in FIG. 1. The first and/or second clamps (1),(2) can be compressed or slid towards each other by movement or sliding along the bar (4) to fit around the outside or sides of the hips and pelvis of the individual. Optional padding attachments (5), including tubing handle (10) and padding can be provided or selected as optionally attached to one or more of the clamps (1),(2) to fit the hips, back, and pelvis of the subject and the pressure points desired. Suitably sized and shaped back-pressure attachments (6) can optionally be used, selected, or provided, and/or adjusted to fit against the hips or pelvis by rotating the threaded bolt (8) that is attached to the back pressure foam attachments (6) through threaded opening in folded portion (7) to apply pressure to the lower back area or pelvis after the first (1) and second (2) clamps are attached to the bar (4) and the $1^{st}$ and $2^{nd}$ padding attachments (5), connected to the clamps (1,2), are placed around the hips and/or pelvis of the subject and compressed to properly fit around the hips and/or pelvis.

As further shown in FIG. 1, the device is constructed by using a bar (4) (including any suitable material, e.g., but not limited to: plastic, metal, and/or polymer, or any combination thereof) as the backbone of the device having a sliding area (4a), such as a slot or channel to slide the first (1) and second (2) clamps onto bar (4), with the adjustable slider (6,7,8) including any suitable mechanism to attach to the backbone, slot or channel, e.g., clamps, gears, springs, screw, bolt, wing-nut, and/or similar attach and release mechanism, or any combination thereof.

Clamp (1) slides up and down the bar (4) while clamp (2) can be fixed. Both clamps (1,2) have an attached tubing handle (10), which can be made of any suitable material, e.g., but not limited to: plastic, metal, foam, rubber, high density polyurethane foam, and/or polymer, or any combination thereof. Attached to clamp (1) is a trigger system (11) to create pressure towards clamp (2). Clamp (1) also includes a trigger release (9) to relieve the pressure.

Padding attachments (5) include exterior padding covering at least a portion of a threaded tube (3) interior including $1^{st}$ or $2^{nd}$ threaded tubing (3) of any suitable material, e.g., but not limited to: plastic, metal, and/or polymer, or any combination thereof, and wherein the padding can include any suitable material, e.g., but not limited to: plastic, foam, rubber, high density polyurethane foam, and/or polymer, or any combination thereof. These padding attachments can optionally be connected, attached, bound, operably attached, or held in place using any suitable element or method, e.g., bolt, screw, bonding with adhesive, interlocking or threaded elements, wrap, tape, adhesive, and shrink wrap or any combination thereof. The padding attachments (5) can optionally slide over the tubing (3) that is attached to the clamps (1,2) to provide strength during compression.

Interchangeable back pressure attachments (6) are constructed using any suitable material, e.g., but not limited to: plastic, metal, steel, foam, rubber, high density polyurethane foam, and/or polymer, or any combination thereof. The frame in the attachments optionally include a threaded bolt (8b), made of any suitable material, e.g., but not limited to: plastic, metal, and/or polymer, or any combination thereof. This bolt can be tightened or loosened to apply different pressures after clamp (1) has been tightened. The bolt threads through the threaded bolt are preferably adjustably connected at one end to the back pressure attachments (6) and also adjustably connected in a middle portion of the threaded bolt (8b) to a threaded opening (8a) that is attached to folded portion (7) that at least partially surrounds and slides along the bar (4) between the first (1) and second (2) clamps, wherein the folded portion (7) is made of any suitable material, e.g., but not limited to: plastic, metal, and/or polymer, or any combination thereof. In an optional implementation, the folded portion (7) is metal or steel that is connected or welded to itself and includes a threaded opening that is configured to receive the threaded bolt (8b), such that the back pressure foam attachment can be placed and secured against pressure points or other suitable portion of the rear lower back or pelvis by screwing or unscrewing the threaded bolt (8) within the threaded opening provided in the folded portion (7). The folded portion (7) is configured to be wrapped around the bar (4) such that the folded portion can move freely side to side upon the bar (4) between the $1^{st}$ (1) and $2^{nd}$ (2) clamps so that pressure can be targeted to different regions of the lower back or pelvis. The different shapes of the attachments (6), e.g., but not limited to, those shown in FIGS. 3A, 3B and 3C, are configured to press against different locations or different pressure points of the lower back or pelvis to relieve pain in the lower back during labor, contractions, or child delivery.

The foregoing is illustrative of the present developments hereof, and is not to be construed as limiting thereof. The developments hereof are defined by the following claims, with equivalents of the claims to be included therein.

What is claimed:

1. A method for reducing pain in the sacrum, hips, and pelvic area of a woman during contractions, labor, and child birth, the method comprising:
   (a) providing a device that applies mechanical pressure directly to pressure points on the outside of the hips, pelvic area, and sacrum of a person experiencing pain in the sacrum, hips, and/or pelvic area during labor, the device comprising:
      (i) a first clamp comprising a first clamping area; a releasable first trigger; a first sliding mechanism; a first locking mechanism; and a first threaded connection;
      (ii) a second clamp comprising a second clamping area; a releasable second trigger; a second sliding mechanism; a second locking mechanism; and a second threaded connection;
      (iii) a lateral bar comprising a sliding area for sliding the first clamp and the second clamp along a length of the lateral bar;
      (iv) a first padding attachment comprising an interior first threaded tubing threaded onto the first threaded connection of the first clamp; the first threaded tubing covered by a first exterior foam; the first padding attachment operably attachable to the first clamp via the first threaded connection; and
      (v) a second padding attachment comprising an interior second threaded tubing threaded onto the second threaded connection of the second clamp; the second threaded tubing covered by a second exterior foam; the second padding attachment operably attachable to the second clamp via the second threaded connection; and
      (vi) an adjustable slider disposed slidably on the lateral bar to move laterally thereon and comprising:
         (A) a folded portion slidable along the lateral bar between the first clamp and the second clamp;
         (B) a threaded opening for a threaded bolt;
         (C) a threaded bolt threaded through the threaded opening and having at one end at least one of one or more interchangeable back pressure foam attachments; and having at an opposite end tightening or loosening portions;
         the adjustable slider being configured to apply different pressures to the sacrum, hips, and pelvic area to relieve pain in the sacrum, hips, and pelvic area by applying pressure to the one of the interchangeable back pressure foam attachments by turning the threaded bolt within the threaded opening, after the first and second clamps have been positioned to apply the pressure to the pressure points on the outside of the hips, pelvic area, and sacrum of the person experiencing the pain in the pelvic area and sacrum areas during labor; and
   (b) applying pressure using the device to the pressure points on the outside of the hips, pelvic area, and sacrum of the person experiencing pain in the hips, pelvic, and/or sacrum areas during contractions, labor, or childbirth, such that the pain in the hips, pelvic area, and sacrum areas during contractions, labor and childbirth is reduced, the applying pressure comprising:
      (i) locking the second clamp adjacent one end of the sliding area of the lateral bar using the releasable second trigger and the second locking mechanism;
      (ii) sliding or providing the adjustable slider over an end of the sliding area of the lateral bar;
      (iii) sliding the first sliding mechanism of the first clamp over the sliding area of the lateral bar using the releasable first trigger and locking the first clamp to the lateral bar using the first locking mechanism, such that the outside of the sacrum, hips, and pelvic area are clamped between the first padding attachment and the second padding attachment; and
      (vi) tightening or loosening the adjustable slider to apply different pressures to the one of the interchangeable back pressure foam attachments, and the first padding attachment and the second padding attachment, and to the hips, pelvic area, and sacrum, after the first and second clamps have been positioned, such that pressure is applied to the pressure points on the outside of the hips, pelvic area, and sacrum of the person experiencing the pain in the pelvic area, hips, and sacrum during labor, such that the pressure applied reduces pain during contractions, labor, and child birth.

2. The method of claim 1, the bar comprising steel.

3. The method of claim 1, the first clamp being configured to slide up and down the bar while the second clamp is fixed to the bar.

4. The method of claim 1, the first or second threaded tubing comprising steel.

5. The method of claim 1, the first or the second releasable trigger comprising a trigger release to unlock the first or second locking mechanisms.

6. The method of claim 1, the foam of the first or second padding attachments comprising polyurethane foam.

7. The method of claim 1, further comprising further comprising the operation of (c) heating the sacrum, lower back, pelvic area, and/or hips of the woman to further reduce the sensation of pain by the woman.

8. The method of claim 1, the method further comprising the operation of (c) vibrating the sacrum, pelvic area, or hips of the woman to further reduce the sensation of pain by the woman.

9. The method of claim 1, the bar comprising plastic, metal, aluminum, fiberglass, rubber, and/or carbon fiber.

10. The method of claim 1, both the first clamp and the second clamp being configured to slide up and down the bar while the second clamp is fixed to the bar.

11. The method of claim 1, the first or second threaded tubing comprising one or more of plastic, metal, aluminum, fiberglass, rubber, and/or carbon fiber.

12. The method of claim 1, the first or the second releasable trigger comprising a trigger lock to lock the first or second trigger and/or locking mechanisms.

13. The method of claim 1, the foam of the first and/or second padding attachments comprising one or more of an open cell foam, a plastic foam, a polymer foam, and/or a compostable foam.

14. The method of claim 1, the operation of (c) heating the sacrum, pelvic area, or hips of the woman to further reduce the sensation of pain by the woman comprises applying one or more of dry, wet, or infrared heat.

15. The method of claim 1, the step of (c) vibrating the sacrum, pelvic area, or hips of the woman to further reduce the sensation of pain by the woman comprising sonic, mechanical, or infrared vibration.

16. The method of claim 1, the pressure being applied for a period of 1 to 120 minutes.

17. The method of claim 1, the pressure being applied for a period of 1 to 30 hours.

18. A device for reducing pain in the sacrum, pelvic area, and hips of a woman during contractions, labor, and child birth, the device configured for applying pressure to pressure points on the outside of the sacrum, hips, and pelvic area, of a person experiencing pain in the sacrum, pelvic area, and hips during labor, the device comprising:
(i) a first clamp comprising a first clamping area; a releasable first trigger; a first sliding mechanism; a first locking mechanism; and a first threaded connection;
(ii) a second clamp comprising a second clamping area; a releasable second trigger; a second sliding mechanism; a second locking mechanism; and a second threaded connection;
(iii) a lateral bar comprising a sliding area for sliding the first clamp and the second clamp along a length of the lateral bar;
(iv) a first padding attachment comprising an interior first threaded tubing threaded onto the first threaded connection of the first clamp; the first threaded tubing covered by a first exterior foam; the first padding attachment operably attachable to the first clamp via the first threaded connection; and
(v) a second padding attachment comprising an interior second threaded tubing threaded onto the second threaded connection of the second clamp; the second threaded tubing covered by a second exterior foam; the second padding attachment operably attachable to the second clamp via the second threaded connection; and
(vi) an adjustable slider disposed slidably on the lateral bar and comprising:
(A) a folded portion slidable along the lateral bar between the first clamp and the second clamp;
(B) a threaded opening for a threaded bolt;
(C) a threaded bolt threaded through the threaded opening and having at one end at least one of interchangeable back pressure foam attachments; and having at an opposite end tightening or loosening portions;
the adjustable slider being configured to apply different pressures to the sacrum, pelvic area, and hips to relieve pain in the sacrum, hips, and pelvic area by applying pressure to the one of the interchangeable back pressure foam attachments by tightening or loosening the tightening or loosening portions by turning the threaded bolt within the threaded opening, after the first and second clamps have been positioned to apply the pressure directly to the pressure points on the outside of the hips, pelvic area, and sacrum of the person experiencing the pain in the sacrum, pelvic area, and hips during labor, such that the pressure applied reduces pain during contractions, labor, and child birth.

19. A method for reducing pain in the sacrum, pelvic areas, and hips of a woman during contractions, labor, and child birth, the method comprising:
providing a device according to claim 18 that applies pressure to pressure points on the outside of the sacrum, hips, and pelvic area, of a person experiencing pain in the sacrum, pelvic area and hips during labor.

* * * * *